(12) United States Patent
Carter

(10) Patent No.: US 7,794,389 B2
(45) Date of Patent: Sep. 14, 2010

(54) ENDOSCOPIC ELEVATOR APPARATUS

(75) Inventor: Matthew P. Carter, Dobson, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 727 days.

(21) Appl. No.: 11/713,919

(22) Filed: Mar. 5, 2007

(65) Prior Publication Data

US 2007/0208219 A1 Sep. 6, 2007

Related U.S. Application Data

(60) Provisional application No. 60/779,182, filed on Mar. 3, 2006, provisional application No. 60/779,181, filed on Mar. 3, 2006.

(51) Int. Cl.
*A61B 1/00* (2006.01)
(52) U.S. Cl. ....................... 600/107; 600/106
(58) Field of Classification Search .............. 600/106, 600/107, 129
See application file for complete search history.

(56) References Cited

U.S. PATENT DOCUMENTS

| | | | |
|---|---|---|---|
| 4,407,273 A | 10/1983 | Ouchi et al. | |
| 4,841,949 A | 6/1989 | Shimizu et al. | |
| 5,343,853 A | 9/1994 | Komi et al. | |
| 5,386,818 A | 2/1995 | Schneebaum et al. | |
| 5,460,168 A * | 10/1995 | Masubuchi et al. | 600/123 |
| 5,707,344 A | 1/1998 | Nakazawa et al. | |
| 5,820,546 A | 10/1998 | Ouchi | |
| 5,899,850 A | 5/1999 | Ouchi | |
| 5,921,971 A | 7/1999 | Agro et al. | |
| 5,938,586 A | 8/1999 | Wilk et al. | |
| 5,938,587 A | 8/1999 | Taylor et al. | |
| 6,827,683 B2 | 12/2004 | Otawara | |
| 7,087,010 B2 * | 8/2006 | Ootawara et al. | 600/104 |
| 2002/0091303 A1 | 7/2002 | Ootawara et al. | |
| 2005/0101836 A1 | 5/2005 | Onuki et al. | |
| 2006/0161046 A1 * | 7/2006 | Ouchi | 600/129 |

FOREIGN PATENT DOCUMENTS

| | | |
|---|---|---|
| EP | 1 764 028 A1 | 3/2007 |
| WO | WO 99/29362 | 6/1999 |
| WO | WO 00/74565 A1 | 12/2000 |
| WO | WO 2006/004053 A1 | 1/2006 |
| WO | WO 2006/113465 A1 | 10/2006 |

\* cited by examiner

*Primary Examiner*—Linda C Dvorak
*Assistant Examiner*—Alireza Nia
(74) *Attorney, Agent, or Firm*—Brinks Hofer Gilson & Lione

(57) ABSTRACT

An endoscopic elevator apparatus cooperable with an insertion tube extending to a distal tip and having enhanced grasping and reduced scraping of an elongate medical device is disclosed. The apparatus comprises an elevator movably attached to the distal tip. The elevator has an inner side formed thereon defining a grasping slot for engagement with the endoscope. The elevator has a surface projection disposed thereon for inhibiting damage to the elongate medical device.

16 Claims, 6 Drawing Sheets

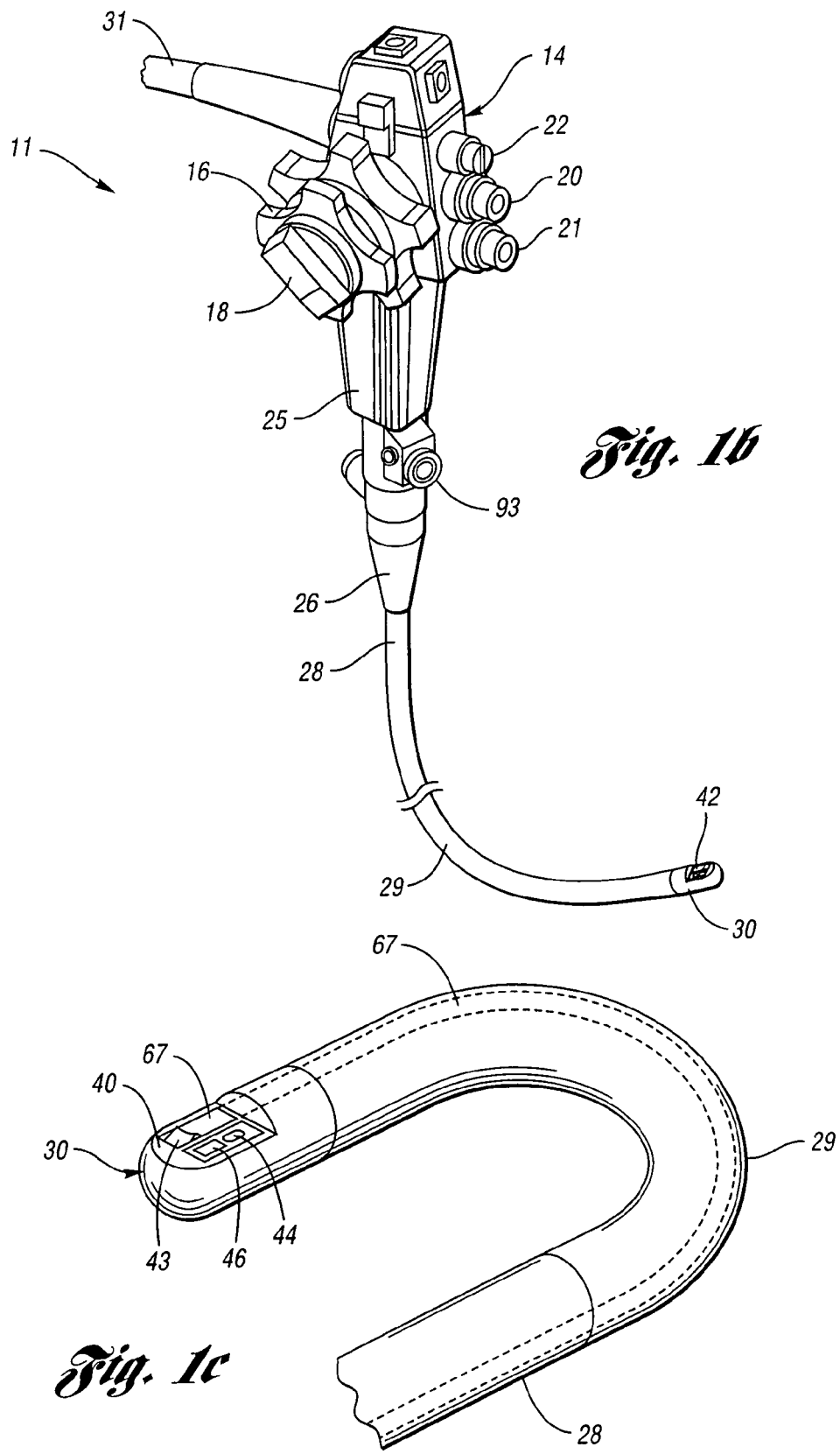

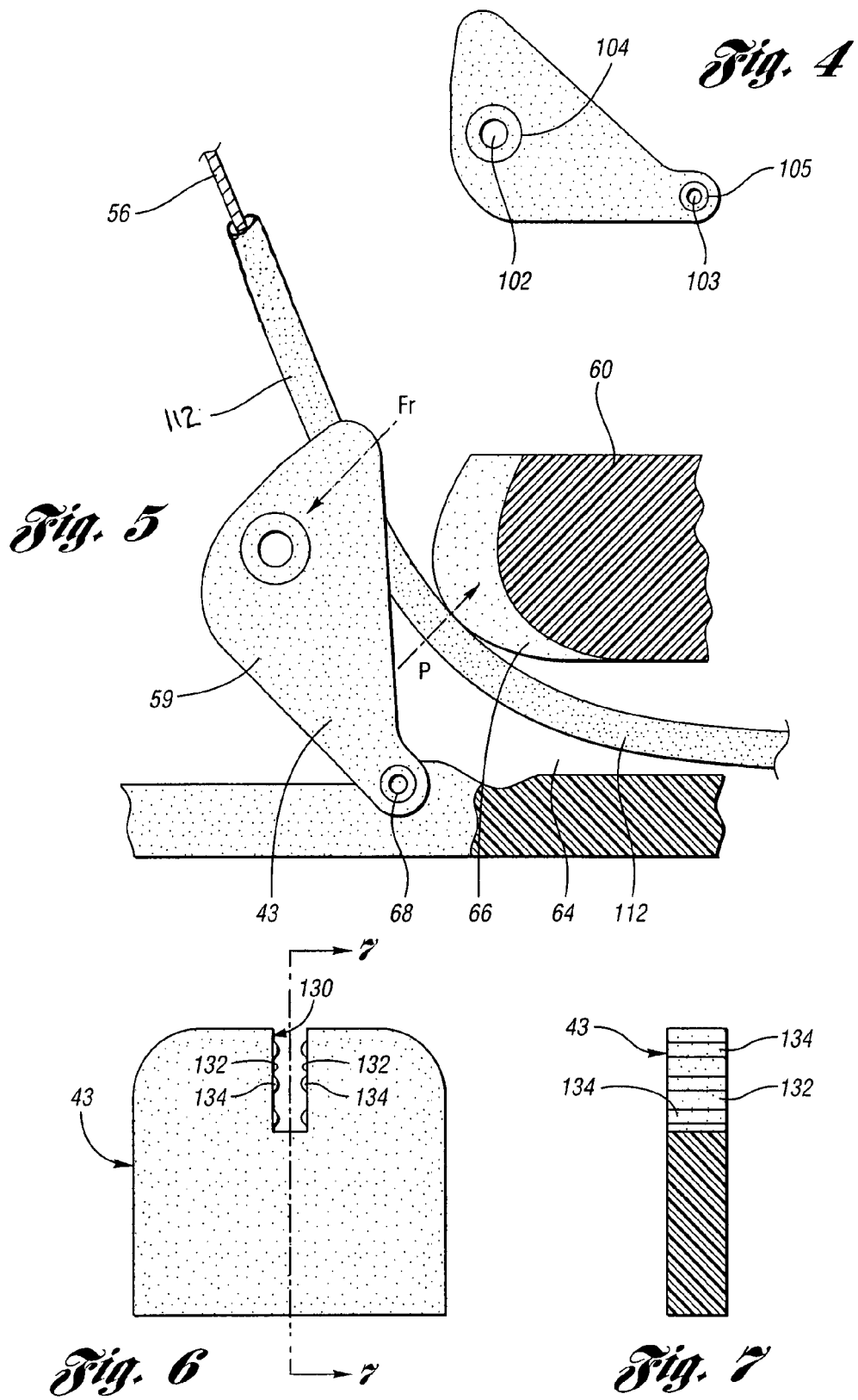

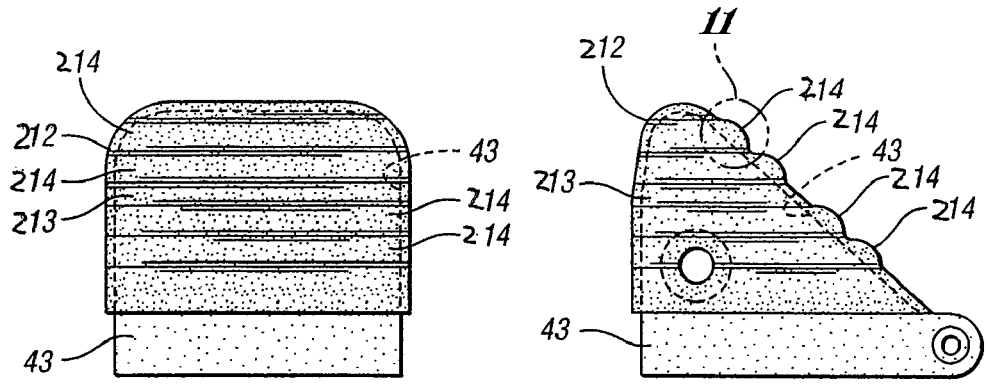
*Fig. 9*                *Fig. 10*
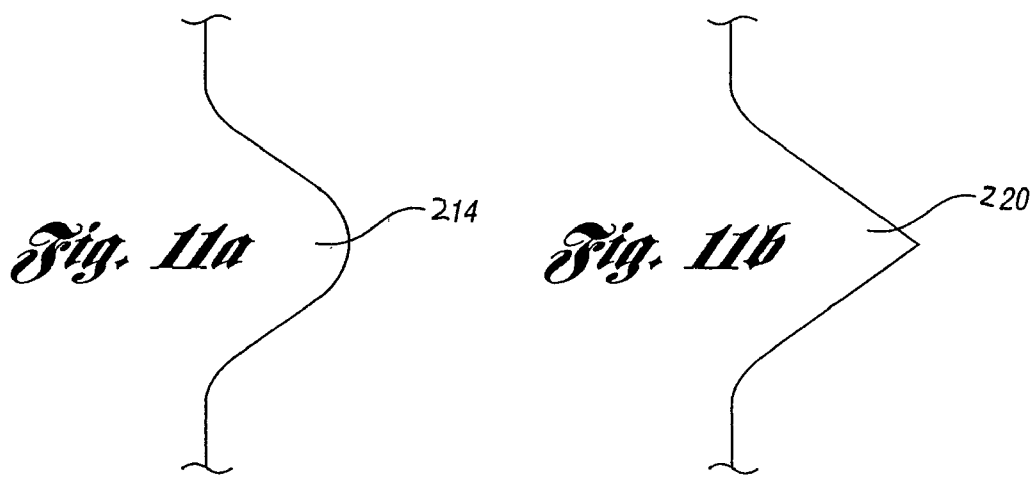
*Fig. 11a*              *Fig. 11b*
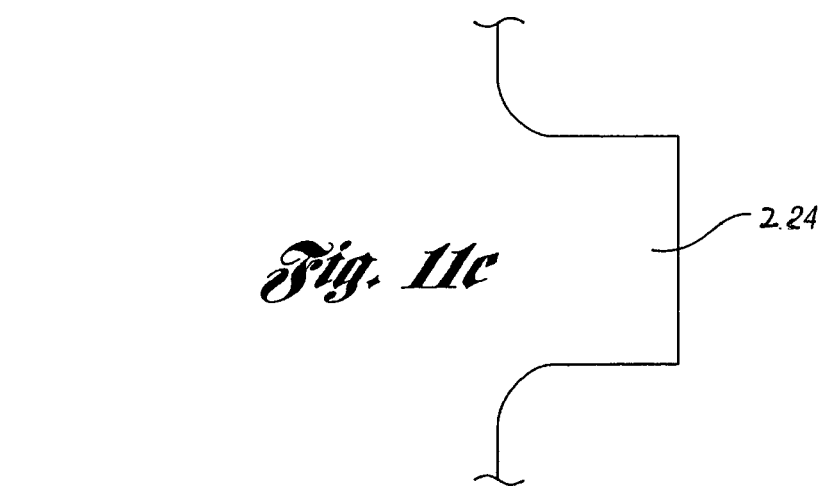
*Fig. 11c*

ENDOSCOPIC ELEVATOR APPARATUS

CROSS-REFERENCE TO RELATED APPLICATIONS

This application claims the benefit of U.S. Provisional Application Ser. No. 60/779,182, filed on Mar. 3, 2006, entitled "ENDOSCOPIC ELEVATOR APPARATUS HAVING A POLYMERIC ELEVATOR WITH A GRASPING SLOT," the entire contents of which are incorporated herein by reference.

This application also claims the benefit of U.S. Provisional Application Ser. No. 60/779,181, filed on Mar. 3, 2006, entitled "ENDOSCOPE HAVING AN ELEVATOR WITH A GRASPING COVER," the entire contents of which are incorporated herein by reference.

FIELD OF THE INVENTION

The present invention relates to medical devices, and more particularly, to endoscopic apparatus having a medical instrument elevator.

BACKGROUND OF THE INVENTION

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments), out of the working channel of the endoscope, a rigid elevator is typically used to orient or deflect the distal end of the wire guide. When the distal end of the wire guide is properly oriented, the wire guide is inserted into the target anatomy.

At this point in the procedure, a catheter or similar treatment instrument can be passed over the wire guide either in a conventional over-the-wire style or in a rapid exchange style to the target anatomy. In order to limit movement of the wire guide relative to the target anatomy, the distal or proximal ends of the guide wire can be locked relative to the endoscope.

Many current endoscopic systems include endoscopes having an elevator used to orient and/or to lock the distal end of the catheter or wire guide. In many of such endoscopes, the elevator includes a v-shaped groove. The v-shaped groove is typically used to guide the catheter or wire guide to a central position relative to the endoscope. The elevator having a v-shaped groove is further used to lock the distal end of the catheter or guide wire.

Endoscopes using a rigid elevator lock and/or a v-shaped groove arrangement, however, may be improved. For example, in many situations, the elevator may tear, scrape, or otherwise affect wire guides or other instruments used therewith. This is particularly a problem with soft, Teflon™-coated wire guides. When such wire guides are positioned within the v-shaped groove of the elevator, even slight axial movement of the wire guide may result in a torn, scraped, or stripped wire guide. Such damage to a wire guide may undesirably require replacing the wire guide during the procedure. This, in turn, undesirably lengthens the overall procedure time and may increase the cost thereof.

Many other endoscopes are provided with rigid, flat-edged elevators. One challenge is that wire guide orientation is difficult to control with flat-edged elevators. Specifically, the wire guide tends to move from side to side relative to the elevator, thereby challenging the physician to insert the wire guide into a target anatomy. Moreover, when flat-edged elevators are used to lock the distal end of an instrument, tearing, scraping, stripping or other undesirable effects on the instrument can also result.

Another issue is that during use the elevator may compress elongate devices such as catheters, thereby preventing the passage of fluids therethrough or impeding the operation of the catheter device.

Thus, there is a need for an elevator design that relatively firmly grasps a elongate medical device and reduces the risk of tearing, scraping, or stripping of devices (e.g., wire guides or catheter) during deployment in a body vessel and allows flow of fluid therethrough during use.

BRIEF SUMMARY OF THE INVENTION

The embodiments of the present invention provide an endoscopic elevator system and an endoscopic assembly having enhanced features for grasping of a medical device, e.g., a catheter or wire guide. The present invention solves some of the current challenges in the endoscope industry. That is, embodiments of the present invention provide a way, during an endoscopic procedure, to maintain a relatively firm grasp of the medical device while reducing the risk of scraping, tearing, or stripping the medical device.

In one embodiment, the present invention provides an endoscopic elevator apparatus cooperable with an insertion tube extending to a distal tip and having enhanced grasping and reduced scraping of an elongate medical device. The apparatus comprises an elevator movably attached to the distal tip. The elevator has an inner side formed thereon defining a grasping slot for engagement with the endoscope. The elevator has a surface projection disposed thereon for inhibiting damage to the elongate medical device.

In another embodiment, the apparatus includes a grasping cover disposed over the elevator. The grasping cover includes a body having an open lip, defining an opening through which the elevator is received. The grasping cover has the surface projection disposed thereon.

The yet another embodiment, the present invention comprises an endoscopic system for reduced scraping of an elongate medical device. The system comprises an insertion tube extending to a distal tip including an elevator movably attached to the distal tip. The elevator has an inner side formed therethrough, defining a grasping slot for engagement with the endoscope. The elevator has a surface projection disposed thereon for inhibiting damage to the elongate medical device.

Further objects, features, and advantages of the present invention will become apparent from consideration of the following description and the appended claims when taken in connection with the accompanying drawings.

BRIEF DESCRIPTION OF THE DRAWINGS

FIG. 1b is a perspective view of the endoscope depicted in FIG. 1b;

FIG. 1c is an elevated view of a distal tip of the endoscope in accordance with one embodiment of the present invention;

FIG. 4 is a side view of an elevator in accordance with one embodiment of the present invention;

FIG. 5 is a cross-sectional view of the tip of the endoscope of FIG. 1, depicting a wire guide secured by an elevator;

FIG. 6 is an elevated view of an elevator in accordance with one embodiment of the present invention;

FIG. 7 is a cross-sectional view of the elevator in FIG. 6 taken along line 7-7 in accordance with one embodiment of the present invention;

FIG. 9 is an elevated view of an elevator according to another embodiment of the present invention;

FIG. 10 is a side view of the elevator in FIG. 6 having engaging ribs according to one embodiment of the present invention; and FIGS. 11a-11c are enlarged side views of the elevator in circle 11 of FIG. 10 in accordance with examples of the present invention.

DETAILED DESCRIPTION OF THE INVENTION

The present invention generally provides an endoscopic elevator and an endoscopic assembly having enhanced features of grasping and reduced scraping of a medical device. Embodiments of the present invention allow a practitioner to relatively firmly grasp the medical device within an endoscope, while reducing the risk of scraping, tearing, or stripping of the medical device (e.g., catheter, wire guide. In one embodiment, a polymeric endoscopic elevator generally comprises inner sides defining a slot within which a medical device (e.g., catheter, wire guide) is disposed. Each of the inner sides has a grasping ridge or rib formed thereon. In another embodiment, the elevator generally includes a polymeric grasping cover disposed over the elevator. The grasping cover includes a body having an open lip defining an opening through which the elevator is received. The grasping cover has the at least one surface projection disposed thereon for enhanced grasping and reduced scraping.

Figure 1A:
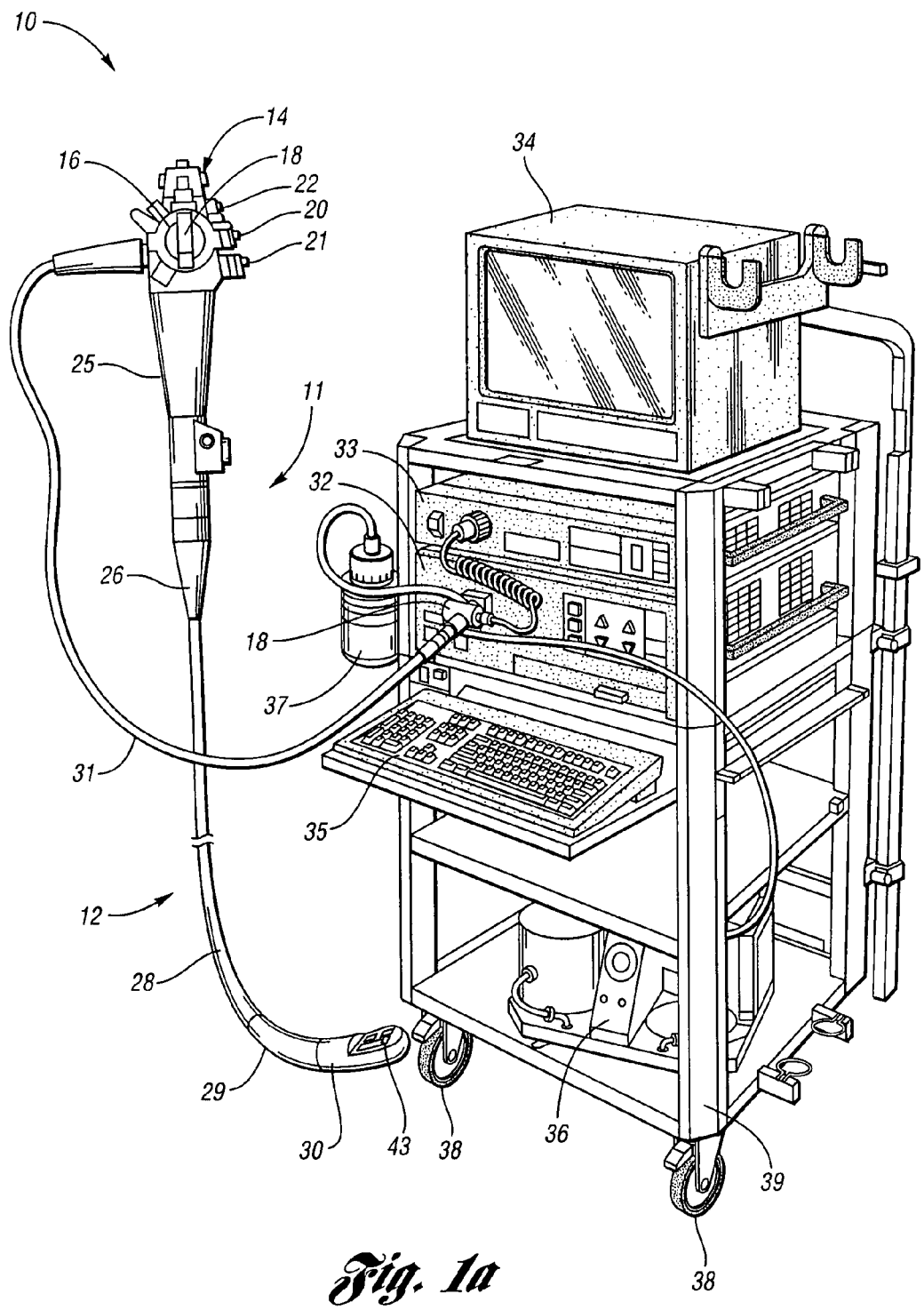
FIG. 1a is a perspective view of an endoscopic system comprising an endoscope in accordance with one embodiment of the present invention.
Figure 2:
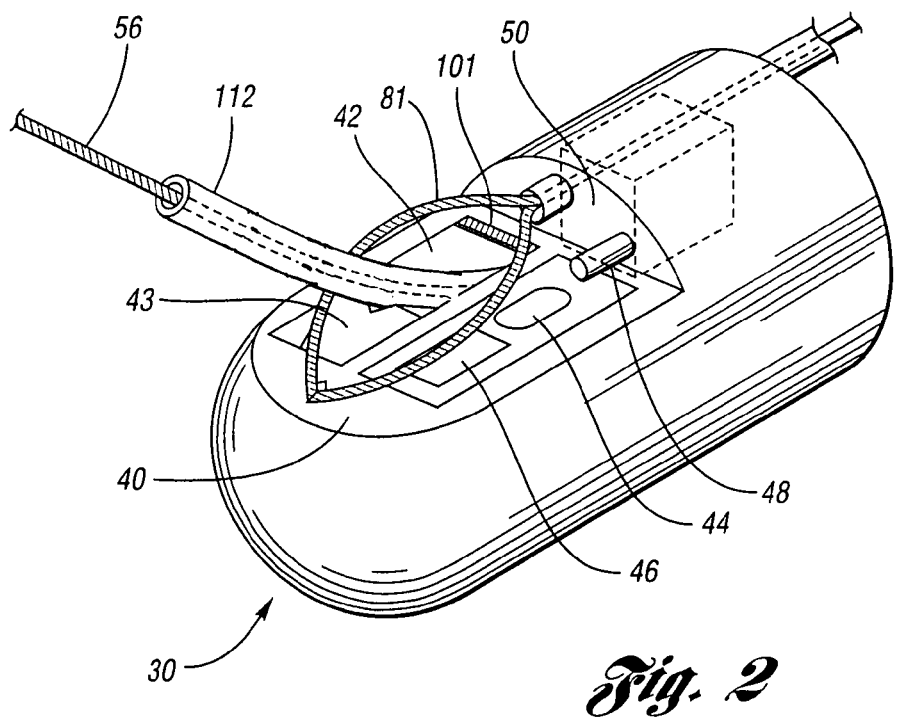
FIG. 2 is an enlarged view of the distal tip of the endoscope in accordance with one embodiment of the present invention.
Figure 3:
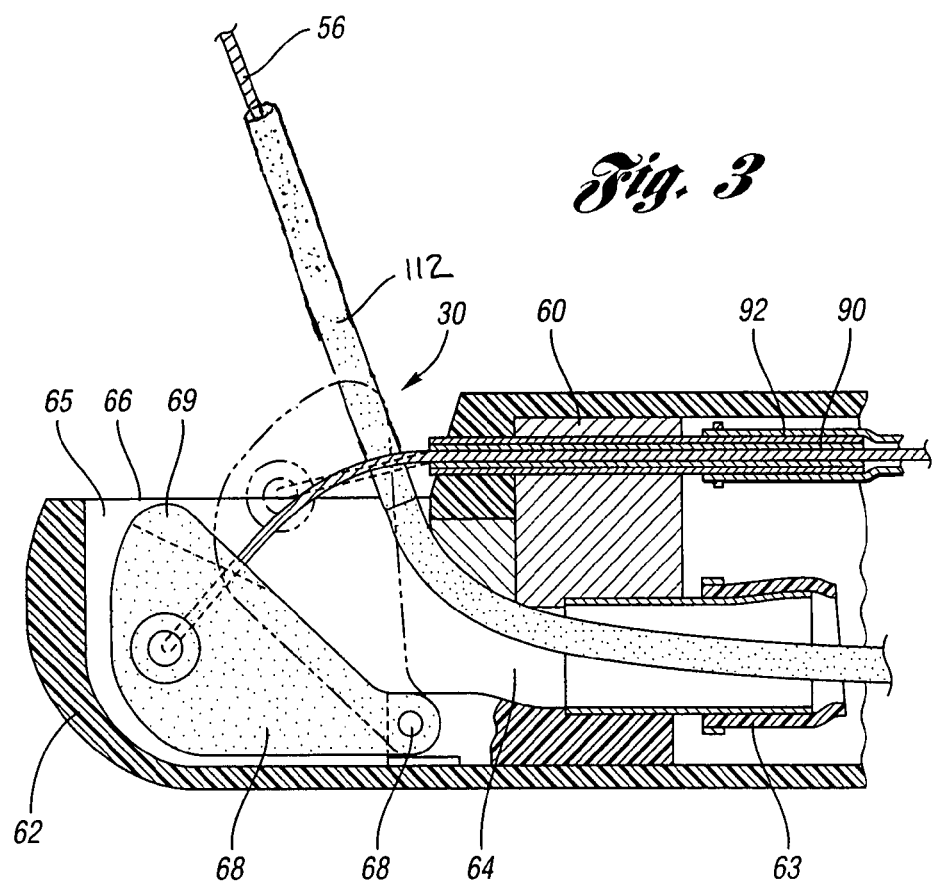
FIG. 3 is a cross-sectional view of the distal tip of the endoscope insertion portion of the endoscope taken along line 3-3.

FIGS. 1-3 illustrate an endoscopic system comprising an endoscope having an elevator with a distal tip. In one example, this system represents a modification to the Olympus V-Scope™. Additional details relating to the endoscopic system discussed herein are described in U.S. Pat. No. 6,827,683, entitled "ENDOSCOPE SYSTEM AND MEDICAL TREATMENT METHOD" issued Dec. 7, 2004 to Takashi Otawara, which is incorporated herein by reference in its entirety.

FIG. 1a illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. The insertion tube 12 has a channel port through which endoscopic units may be disposed. In one embodiment, endoscopic units disposed in one of the ports may include one embodiment of an improved elevator having a distal tip.

As shown in FIGS. 1a and 1b, the endoscope 11 further includes a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication with one of the channel ports 13 of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure. The endoscope, in combination with the elevator having the distal tip, reduces the risk of tearing or scraping of the wire guide.

In this embodiment, the insertion tube 12 comprises an operating portion 25 connected to the control system 14 and extending to an insertion protecting member 26. A control system 14 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 14. On the other end, the cord 31 has a connector 18 attached thereto. The connector 18 is in communication to a light guide tube and electrical contact, and is connected to a light source apparatus 32 and an image processing apparatus 33 (external devices). These external devices may include a monitor 34, an input keyboard 35, a suction pump apparatus 36, irrigation bottle 37, and other suitable apparatus that are installed on a rack 39 equipped with rollers 38.

As shown in FIGS. 1c and 2, a cutout 40 is formed on the outer circumferential surface of the tip 30. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to be sprayed towards the outer surface of the objective lens 44 to clean the lens surface.

FIGS. 1c and 2 further illustrate the elevator 43 comprising a grasping slot 91 in accordance with one embodiment of the present invention. The grasping slot may take on any suitable shape or form for grasping of a medical device. In this embodiment, the grasping slot 91 is narrowly formed by inner sides 92 that define the grasping slot 91 formed through the elevator 43. Preferably, the grasping slot 91 is centrally formed through the elevator 43 for receiving a medical device (e.g., catheter or wire guide) and grasping the device during operation of the endoscope.

As depicted in FIG. 2, tip 30 further includes a guide catheter 52 and a wire guide 56 disposed through the guide catheter 52. The tip 30 further includes an elevator 43 configured to receive the guide catheter and/or wire guide for elevating the guide catheter 52 or wire guide 56. As will be described in greater detail below, the elevator 43 is comprised of polymeric material and has a grasping slot formed therethrough for enhanced grasping and reduced scraping purposes.

The elevator 43 is pivotally attached to the tip 30 and is configured to receive the medical instrument (e.g., catheter or wire guide) for elevating the medical instrument. As shown in FIG. 3, the distal tip houses the elevator 43 in channel opening 42. The elevator 43 is used to orient medical instruments such as a catheter. As discussed in greater detail below, this is accomplished by engaging the medical instrument and pivoting away from the distal tip thereby laterally moving the distal end of the medical instrument away from the distal tip. The elevator 43 thus secures the distal end of the medical instrument relative to the endoscope. That is, as the medical instrument is received in slot 91 of the elevator 43, the medical instrument laterally moves relative to the tip 30 when the elevator 43 pivots therefrom.

FIG. 3 illustrates that the endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is disposed adjacent the working channel 63, which acts as a passageway for the insertion of the medical instrument, e.g., wire guide or catheter. In this embodiment, a channel 67 (FIG. 1c) is formed through the tip 30 such that the tip opening of the treatment instrument is able to be disposed through channel opening 42.

FIG. 3 further illustrates an elevator wire 90 connected to the elevator 43. In this embodiment, the elevator wire 90 is located at the operating portion 25 and extends through a guide tube 92 and a guide pipe 93 connected to the guide tube 92. The elevator wire 90 is in mechanical communication with the control system 14 so that manipulations at the control system 14 result in movement of the elevator wire 90 relative to the endoscope. FIG. 3 depicts (in phantom) movement of the elevator 43 when the elevator wire 90 is actuated at the control system 14, moving the position of the elevator 43 about the elevator turning support 68 as the elevator wire 90 is retracted or pulled.

In this embodiment, the elevator 43 is moved about the elevator turning support 68 by manipulating or actuating the control system 14 to pull or retract the elevator wire 90. As shown in FIG. 5, the result moves the wire guide 56 in the direction of the arrow P and pushes the elevator 43 against the cuff 60. Because the wire guide 56 is formed from a relatively axially stiff material, it tends to remain straight when pushed against the cuff 60, creating a reactive force in the direction of the arrow Fr in FIG. 5. By means of this reactive force, the wire guide 56 is pressed against the slot 91. Moreover, as the elevator 43 and the cuff 60 press against one another, the wire guide is secured.

In another embodiment, FIGS. 4 and 5 illustrate the elevator 43 having a transverse passageways 102 and 103 formed therethrough, each having optional metal sleeves 104 and 105, respectively, disposed thereon. The metal sleeves are configured to provide transverse rigidity to the elevator. The proximal end of the elevator 43 is attached so as to pivot around the elevator turning support 68 provided to the cuff 60.

The elevator 43 is preferably comprised of polymeric material. The polymeric material may include polytetrafluoroethylene (PTFE), polyethylene, polypropylene, perfluoroelastomer, fluoroelastomer, nitrile, neoprene, polyurethane, silicone, styrene-butadiene, rubber, or polyisobutylene, or a mixture thereof. The polymeric material aids the elevator in relatively firmly grasping the medical device while reducing the risk of tearing, scraping, or striping of the medical device.

FIG. 6 illustrates the elevator 43 comprising a grasping slot 130 in accordance with one embodiment of the present invention. The grasping slot may take on any suitable shaped or form for grasping of a medical device. In this embodiment, the grasping slot 130 is narrowly formed by inner sides 132 that define the grasping slot 130 through the elevator 43. Preferably, the grasping slot 130 is centrally formed through the elevator 43 for receiving a medical device (e.g., catheter or wire guide) and grasping the device during operation of the endoscope.

FIGS. 6 and 7 illustrate the elevator having inner sides 132 in accordance with one embodiment of the present invention. As shown, inner sides 132 include side surface projections 134 formed thereon. In this embodiment, side surface projections 134 are ridges or ribs that are oppositely formed laterally across each of the inner sides. Of course, the side surface projections may be formed on either or both of the inner sides, in any suitable shape, and in staggered configuration. For example, the inner surface projections may be formed longitudinally or in various patterns without falling beyond the scope or spirit of the present invention.

In use, the control system of the endoscope may be manipulated to actuate the elevator, moving the elevator to engage the medical device, e.g., catheter or wire guide. By force, the medical device is worked through the grasping slot 130 of the elevator 43, thereby engaging the medical device with the inner sides 132 of the elevator 43. The side surface projections 134 engage the device and, due to the polymeric material of the elevator 43, partially deform and absorb the device to reduce the risk of scraping thereof. In use, the side surface projections 134 receive the medical device when disposed within the slot for enhanced grasping and reduced risk of scraping of the medical device.

In addition to reducing the risk of tearing and scraping, the formation of the slot allows a physician to more firmly grasp and secure the distal end of an instrument or wire guide relative to other endoscopes. To avoid further stripping or otherwise damaging an instrument or wire guide, cuff 60 can be provided with an elastomeric outer surface 66 (see FIG. 3).

Figure 8A:
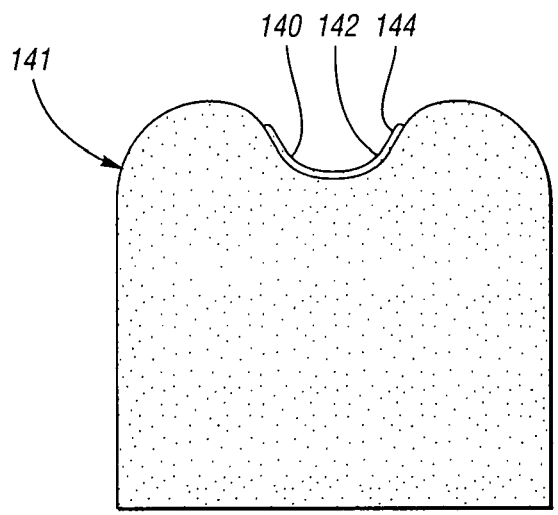
FIGS. 8a-8c are elevated views of elevators in accordance with other embodiments of the present invention.
Figure 8B:
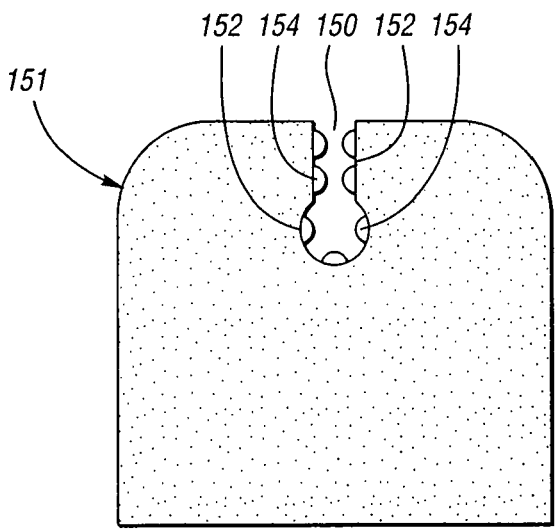
Figure 8C:
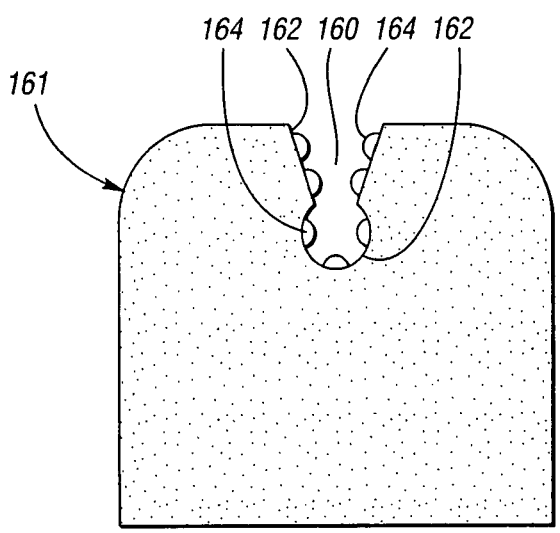

FIGS. 8a-8c further illustrate various configurations of grasping slots 140, 150, 160 formed through the elevator. As mentioned above, the grasping slots may take on any desirable or suitable shape for grasping of a medical device of an endoscope. For example, as shown in FIG. 8a, the grasping slot 140 of elevator 141 may have a cross-sectional shape that is semi-circular or arcuate. In this embodiment, the grasping slot 140 has an arcuate side 142 that defines the grasping slot 140. As shown, the arcuate side 142 includes surface projections 144 formed thereon for grasping the medical device.

FIG. 8b illustrates grasping slot 150 of elevator 151 in accordance with another embodiment of the present invention. As shown, the grasping slot 150 has inner and arcuate sides 152 that define the slot 150. In this embodiment, the sides 152 include surface projection 154 formed thereon for grasping the medical device. In this embodiment, the grasping slot 150 takes on a keyhole shape, having relatively narrow planar sides 151 and widening to an arcuate side 153. In use, the medical instrument, e.g., a catheter or a wire guide, may be worked between the planar sides 151 and received by the arcuate side 153. As shown, the surface projections 154 disposed immediately proximate the arcuate side 153 on the planar sides serve to hold or biased the medical instrument within the grasping slot 150 against the arcuate side 153. This provides enhanced grasping of the medical instrument within the apparatus.

FIG. 8c illustrates grasping slot 160 of elevator 161 in accordance with yet another embodiment of the present invention. As shown, the grasping slot 160 has tapered and arcuate sides 162 that define the slot 160. In this embodiment, the sides 162 include surface projections 164 formed thereon for grasping the medical device. In this embodiment, the grasping slot 160 once again takes on a keyhole shape, but having planar sides 161 that flare outwardly to receive a medical instrument such as a catheter or a wire guide. As shown, the planar sides 161 then extend to an arcuate side 163. In use, the medical instrument may be worked between the planar sides 161 and received by the arcuate side 163. As shown, the surface projections 164 that are disposed immediately proximate the arcuate side 163 on the planar sides serve to hold or biased the medical instrument within the grasping slot 160 against the arcuate side 163. This provides enhanced grasping of the medical instrument within the apparatus.

FIG. 9 illustrates the elevator 43 comprising a grasping cover or tip 212 disposed on the elevator 43 in accordance with another embodiment of the present invention. In this embodiment, the tip 212 is disposed over the elevator 43 and adhered thereon by any suitable means, e.g., sonic bonding, thermal bonding, or adhesive bonding. As shown, the tip 212 comprises a body 213 having a plurality of lateral ridges or ribs 214 formed thereon. The body 213 has an open lip 215 defining an opening 216 through which the elevator 43 is received. The body 213 is disposed on the elevator 43 with at least one and preferably a plurality of surface projections or ridges 214 positioned thereacross to receive and contact the device. The surface projections 214 may be formed across the body 213 in any suitable manner, e.g., laterally or longitudinally thereacross.

The grasping cover or tip 212 may be made of any suitable material that will cooperate with the device to absorb and deform when in contact therewith, thereby reducing the risk of tearing or scraping of the wire guide. Preferably, the grasping cover 212 is made of polymeric material. For example, the grasping cover 212 may be made of at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

As shown in FIGS. 9 and 10, the lateral ridges 214 are configured to contact and engage the device, e.g., wire guide or catheter, within the endoscope during usage thereof. The lateral ridges 214 aid in retaining and guiding the wire guide 56, while also reducing the risk of tearing or scraping the wire guide. This is accomplished due to the lateral structure of the ridges 213 and the composition thereof. The ridges 214 may take on any desirable or suitable formation to contact the device (e.g. wire guide).

In addition to reducing the risk of tearing and scraping, the tip 212 allows a physician to more firmly grasp and secure the distal end of an instrument or wire guide relative to the endoscope as compared to endoscopes having bare, rigid elevators. To avoid further stripping or otherwise damaging an instrument or wire guide, cuff 60 can be provided with an elastomeric outer surface 66 (see FIG. 3).

FIGS. 11a-11c further illustrate various configurations of ridges or ribs 214, 220, 224, respectively, formed on the elevator. As mentioned above, the ridges 214 may take on any desirable or suitable shape for contact with the wire guide. As shown in FIGS. 11a-11c for example, the ridges 214, 220, 224 may have a cross-sectional shape that is semi-circular or arcuate (FIG. 11a), triangular (FIG. 11b), or rectangular (FIG. 11c).

While the present invention has been described in terms of preferred embodiments, it will be understood, of course, that the invention is not limited thereto since modifications may be made to those skilled in the art, particularly in light of the foregoing teachings.

The invention claimed is:

1. An endoscopic elevator apparatus cooperable with an insertion tube extending to a distal tip and having enhanced grasping and reduced scraping of an elongate medical device, the apparatus comprising:

an elevator movably attached to the distal tip, the elevator having an inner side formed thereon defining a grasping slot for engagement with the elongated medical device, the elevator having a surface projection disposed thereon for inhibiting damage to the elongate medical device: and a grasping cover disposed directly on and adhered to the elevator, wherein the grasping cover includes a body having an open lip defining an opening within which the elevator is received, the surface projection being disposed on the grasping cover.

2. The apparatus of claim 1 wherein the surface projection is disposed on the inner side of the elevator.

3. The apparatus of claim 1 wherein the surface projection is a plurality of surface projections formed on the inner side of the elevator.

4. The apparatus of claim 1 wherein the surface projection is formed laterally across the inner side of the elevator.

5. The apparatus of claim 1 wherein the surface projection is formed longitudinally across the inner side of the elevator.

6. The apparatus of claim 1 wherein the grasping cover comprises a plurality of ridges.

7. The apparatus of claim 6 wherein the each ridge is formed laterally across the body relative to the elevator.

8. The apparatus of claim 1 wherein the inner side of the elevator comprises an edge adjacent to the grasping slot, and further wherein the surface projection is configured so that the surface projection inhibits contact between the elongate medical device and the edge.

9. The apparatus of claim 1 wherein the surface projection projects into the grasping slot and is configured to inhibit damage to the elongate medical device.

10. An endoscopic system for reduced scraping of an elongate medical device, the system comprising:

an insertion tube extending to a distal tip including an elevator movably attached to the distal tip, the elevator having an inner side formed thereon defining a grasping slot for engagement with the elongate medical device, the elevator having a surface projection disposed thereon for inhibiting damage to the elongate medical device, the insertion tube further including a grasping cover disposed directly on and adhered to the elevator, wherein the grasping cover includes a body having an open lip defining an opening within which the elevator is received, and further wherein the at least one surface projection is disposed on the grasping cover.

11. The system of claim 10 wherein the surface projection is disposed on the inner side of the elevator.

12. The system of claim 10 wherein the surface projection is a plurality of surface projections formed on the inner side of the elevator.

13. The system of claim 10 wherein the surface projection is formed laterally across the inner side of the elevator.

14. The system of claim 10 wherein the surface projection is formed longitudinally across the inner side.

15. The system of claim 10 wherein the grasping cover comprises a plurality of ridges.

16. The system of claim 15 wherein the each ridge is formed laterally across the body relative to the elevator.

* * * * *